(12) United States Patent
Milverton

(10) Patent No.: US 6,620,098 B1
(45) Date of Patent: Sep. 16, 2003

(54) DEVICE FOR DILATING A PUPIL AND/OR MAINTAINING A PUPIL IN A DILATED STATE

(75) Inventor: John Milverton, Auburn (AU)

(73) Assignee: Milvella PTY LTD, Epping (AU)

(*) Notice: Subject to any disclaimer, the term of this patent is extended or adjusted under 35 U.S.C. 154(b) by 0 days.

(21) Appl. No.: 09/856,990
(22) PCT Filed: Dec. 2, 1999
(86) PCT No.: PCT/AU99/01090
§ 371 (c)(1), (2), (4) Date: Oct. 2, 2001
(87) PCT Pub. No.: WO00/32141
PCT Pub. Date: Jun. 8, 2000

(30) Foreign Application Priority Data

Dec. 3, 1998 (AU) .................... PP7473

(51) Int. Cl.$^7$ ................................. A61F 9/07
(52) U.S. Cl. ......................... 600/236; 600/208
(58) Field of Search ................. 600/236, 208, 600/209, 210, 215; 606/107

(56) References Cited

U.S. PATENT DOCUMENTS

| 4,387,706 A | * | 6/1983 | Glass | 600/208 |
| 4,782,820 A | * | 11/1988 | Woods | 600/208 |
| 5,163,419 A | * | 11/1992 | Goldman | 600/206 |
| 5,267,553 A | | 12/1993 | Graether | 128/20 |
| 5,374,272 A | * | 12/1994 | Arpa et al. | 606/107 |

FOREIGN PATENT DOCUMENTS

WO  WO 96/29965  10/1996

OTHER PUBLICATIONS

Derwent Abstract Accession No. 134368/19, Class P32, SU 1258405 A (Lengd Doctor Refres), Sep. 23, 1986.

* cited by examiner

Primary Examiner—Cary E. O'Connor
(74) Attorney, Agent, or Firm—Gottlieb Rackman & Reisman, P.C.

(57) ABSTRACT

The present invention consists in a pupil dilating device (1) for dilating a pupil and/or maintaining a pupil in a dilated state, said device (1) being generally hook shaped in plan view so as to define an open ended arcuate iris engaging body portion (2) having a distal free end (3) and at or adjacent the other of said ends (5) an integral positioning arm (4) extending outwardly in a generally radial direction therefrom, the positioning arm (4) being sized to extend in use beyond the outer periphery of the iris; said body portion (2) including: an iris engaging formation or formations (6, 7) being adapted to receive and retain the inner peripheral edge of an iris in an expanded state; and, at least one instrument engaging formation (11) at or adjacent said distal free end (3) to enable contraction of the body portion (2) to facilitate engaging location within the iris.

35 Claims, 4 Drawing Sheets

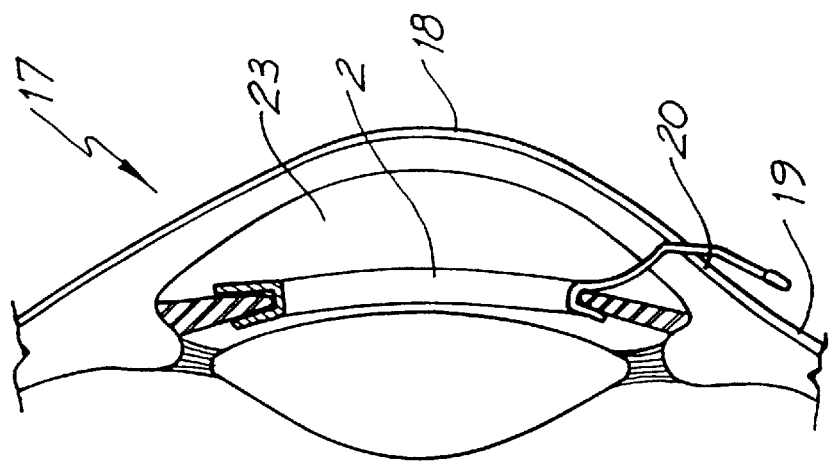
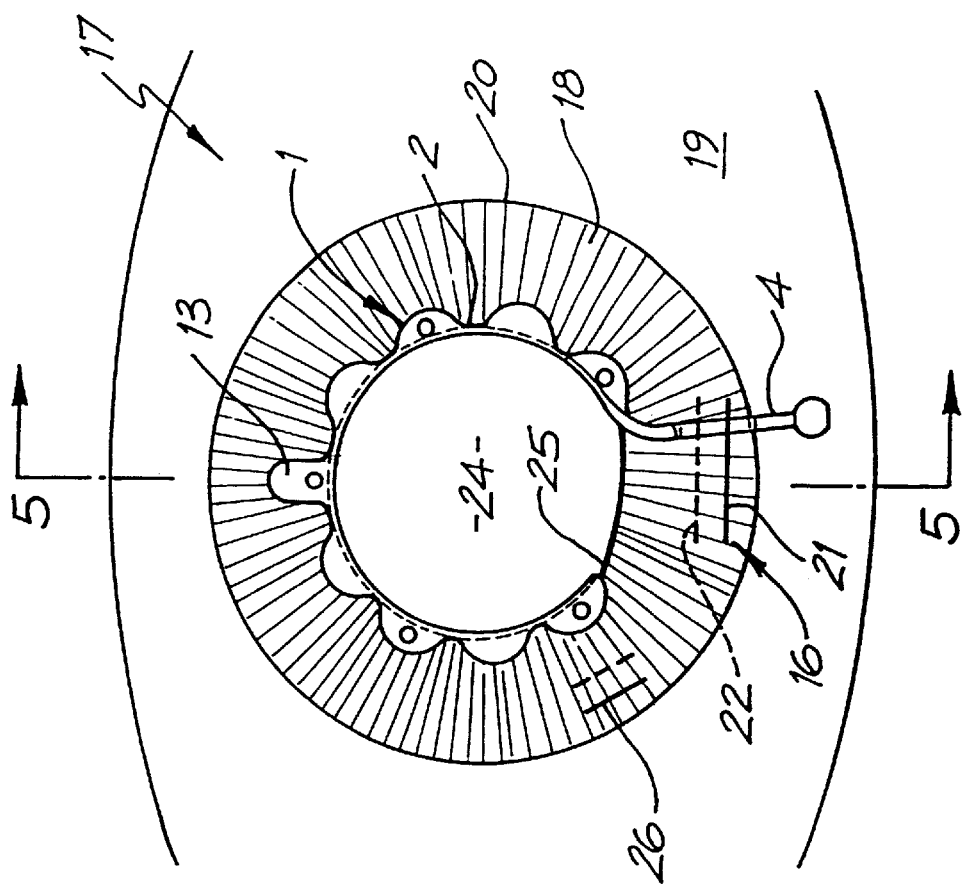

DEVICE FOR DILATING A PUPIL AND/OR MAINTAINING A PUPIL IN A DILATED STATE

The present invention relates to a device for dilating a pupil and/or maintaining a pupil in a dilated state.

The invention has been developed primarily for use in ophthalmic surgery and will be described hereinafter with reference to this application.

BACKGROUND OF THE INVENTION

It is advantageous in many ophthalmic procedures for the pupil to be dilated as much as possible, that is for the iris to be retracted toward the outer edges of the eye. This normally occurs automatically when the eye is deprived of bright light, for example, in dark rooms or at night.

When performing ophthalmic operations, such as inserting an intra-ocular contact lens (ICL), in the posterior chamber, a dilated iris and pupil gives the surgeon a larger area to manipulate the ICL into position. The lens in the eye and its enclosing capsule are delicate structures that may be easily damaged by excessive contact pressure and shock. By maximising the area available to the surgeon there is a reduction in the risk of damaging the iris or human lens or other components of the eye due to unintentional contact with the various surgical instruments.

Retinal surgery involves operating on the retina on the back of the eye while occasionally viewing the retina inside the eye through the pupil. Again a large pupil is a definite advantage for the surgeon during this difficult procedure. Accordingly, maximising the dilation of the iris is of great assistance.

Cataract surgery involves replacing the natural human protein lens inside the eye with an artificial lens. This is usually done because the natural lens has degraded over time from the effects of ultra-violet rays and ageing such that the lens is no longer clear.

In some countries, the present procedure for removing the natural lens involves cutting a semicircle around the edge of the cornea of the eye folding back the resultant flap and physically removing the lens from its enclosing capsule through the iris. The lens is then replaced with a new relatively rigid artificial lens, the cornea returned to its original position and sutured into place. Recovery from this procedure is quite slow and the sutures may subsequently need to be removed.

In most Western countries and Japan, a more advanced procedure is performed involving an ultrasonic fractionator instrument known as a phaco-emulsifier. In this technique the pupil is usually dilated using a topical drug in the form of eye drops and an incision about 3 mm wide is made in the periphery of the cornea. The anterior chamber is inflated with a "visco-elastic" material to keep the anterior chamber fully formed and deep. A tool is introduced through this incision to tear away the anterior capsule covering the lens. The phaco-emulsifier is then introduced through the incision and used to break up the lens. The pieces being sucked out by the phaco-emulsifier and any remnants are drawn out by irrigation/aspiration. The new lens made of foldable material is then introduced through the wound and unfolded into place. The visco-elastic is then sucked from the eye and the procedure is complete. Stitching is not necessary and the patient need only stay overnight or may even be able to return home immediately. This technique is much less traumatic to the eye and much less costly in hospital stay and recuperative therapy.

About one in five patients do not achieve sufficient pupil dilation with topical drugs. Also such eye drops can wear off during an operation resulting in the iris contracting and reducing the pupil size during surgery. This complicates the removal of any lens remnants during and after phaco-emulsification as it is not possible to see inside the entire lens capsule when a portion of it is covered by the iris. Without sufficient pupil dilation, removal of the lens remnants is done by "feel" relying heavily on the experience of the surgeon. Experience has shown that thorough capsular "clean up" of the remnants significantly reduces the need for secondary clean up procedures following cataract surgery.

Insufficiently dilated pupils are also prone to damage from the tip of the phaco-emulsifier. With a small pupil there is a greater likelihood that the phaco-emulsifier tip will touch the inner edge of the iris during emulsification of the lens and cause permanent damage to the iris structures. This is most likely to occur at the inner edge of the iris diametrically opposed to the incision.

A number of physical and therefore surgically more complicated measures can be used to dilate the pupil and maintain it in a dilated state.

One method involves making four minor incisions at roughly 90° intervals around the periphery of the cornea and inserting a small hook-like apparatus through each incision. The hooks engage with the inner circumferential edge of the iris and when retracted, pull the iris outwards to define an enlarged substantially square shaped opening. Another physical method, known as sphincterotomy, involves making an incision into the cornea through which a blade is passed that makes radial cuts into the iris itself, thus allowing the iris to dilate and expose more of the lens. Both the above methods add extra time to the total operation time and the latter involves considerable risk of damage to the patient's iris. Moreover, the damage done in segmenting the iris during a sphincterotomy is irreversible and results in a permanently disfigured iris.

More recent advancements have included the use of generally annular dilating devices. These are usually made from resilient polymeric materials which are contractible to enable insertion through a small incision in the cornea, sclera or limbus and positioning within the iris, the resilient nature of the material acting upon placement to urge and maintain the iris outwardly into a dilated state. These types of prior art dilating devices can be divided into three separate categories.

The first category comprises dilating devices which in their expanded states generally form a complete annulus having surfaces thereon adapted to engage the inner edge of the iris. Examples of such devices are shown in U.S. Pat. No. 4,782,820 (Woods), U.S. Pat. No. 5,267,553 and 5,322,054 (Graether) and U.S. Pat. No. 4,387,706 (Glass).

The Glass device comprises a complete annular ring having a generally 'L' shaped cross section defining an inner axial wall and a posterior flange for seating behind the iris. The dilator is deformable via a pair of opposed pinions provided on the posterior flange. These pinions enable the dilator to be compressed to an oval configuration by the use of forceps to facilitate positioning of the device within the pupil. However, given the relatively rigid nature of the flanged structure and the absence of any means to retain the dilator in a direction parallel to the central axis of the iris, it is understood that practical use of this device in terms of both insertion into the anterior chamber of the eye and subsequent location within the iris would be extremely difficult if not impossible. This view is probably supported by the fact that it appears this design did not materialise into a commercially successful form.

The Graether patents then go on to describe a pupil expander that is generally 'U' shaped in-cross section forming an incomplete annulus, the ends of which are joined by a flexible connecting strap to make a complete circle. In use the expander is deformed into an elongated shape for insertion into the eye via a scieral incision. Elongation is preferably achieved by use of a specially designed jig which aligns the elongated 'U' shaped side walls for sliding onto special forcep tips. While it appears the 'U' shaped channel structure goes some way to addressing the iris retainment problem of Glass, its use is still a slow and awkward procedure and necessitates during insertion severe deformation of the iris into a "cat" like elongate slit which is potentially damaging to the iris.

Woods teaches what may well have been a further improvement over Glass, describing a device also having an elongated arcuate, flexible, resilient body that is generally "U"-shaped in cross section to define an iris receiving side wall, the ends of the body being slidably inter-engaged into a circular ring like structure. A drawstring is provided for manually contracting the body for initial placement within the iris. Arguably the feature of circumferential contraction as opposed to oval deformation may theoretically be advantageous in relation to engaging the device with the iris. However, it is believed that the manufacture and operation of such a device incorporating a draw string contracting mechanism would be extremely difficult, and that its use during ophthalmic procedures would be time consuming and not necessarily reliable. For example the difficulties associated with insertion into the anterior chamber of the eye have not been addressed and nor have means been described for ensuring accurate positioning of the heavily flanged and thereby reasonably rigid device into full engagement with the inner peripheral edge of the iris. Again there does not appear to have been any successful commercialisation of the Woods device to date.

The second category comprises resilient devices that are not fully circular in plan but are generally "U" or "C"-shaped thereby defining an incomplete annulus or similar shape. Examples of such devices include that described in U.S. Pat. No. 5,163,419 (Goldman) and a commercially available pupil dilating device known as the "Schlosshardt" design produced by "Morscher".

The Goldman device is generally "U"-shaped in plan and can be considered to comprise two separate arm portions connected by an intermediate hinge section. The hinge section enables folding of the device for insertion through a corneal incision and for contraction of the device for placement within the pupillary opening. Iris engaging slots or channels are provided at the hinge and the distal ends only of the two arm members. It is believed this would be hard to accurately engage with the iris and further would be readily prone to dislodgment due to fluctuations of pressure that occur during phaco-emulsification.

Similarly, the Morscher Schlosshardt design is generally "C"-shaped in plan, again having iris engaging and retaining formations only at selected spaced intervals around the periphery. Both of the devices include various instrument engaging formations to enable contraction of the device.

The open ended nature of these second category of dilator devices, or at least the Morscher design, may possibly enable easier insertion via the corneal or scleral incision, in that devices could in theory be 'dialled' into the anterior chamber of the eye without the need for prior folding or deformation of the device to facilitate insertion. However, once these devices are in the anterior chamber of the eye, two or more instruments are required for accurate placement and positioning of the device within the pupillary opening. Commercial videos demonstrating use of the Morscher device show that time and dexterity is required for successful manipulation of these devices and that the usual procedure is to rotate the dilator into the iris. This tends to apply a shear force to the iris causing substantial deformation and risk of damage.

The third group includes that described in the applicant's earlier application WO 96/29965 which describes therein various embodiments of devices all comprising a resilient generally arcuate body portion adapted to engage and retain the iris in a dilated state, from the open ends of which two integrally formed positioning arms extend generally radially outwardly. The arms are sized so that the distal ends of the arms during the operation remain external to the eye. In use, the two armed ring is folded or otherwise compressed for insertion through the incision in the cornea, after which the arms are manipulated externally to help in the positioning of the body portion within the pupillary opening. This can be assisted with the aid of suitable additional instruments such as Fenzl hooks and the like.

The addition of the positioning arms was found to greatly assist the process of insertion and removal from the iris and general handling of the device during the operation. However, problems were still encountered during the practical implementation of the design in relation both to the initial insertion of the device into the eye and the subsequent manipulation of the device into position in the iris.

In summary therefore there is still a need for an improved dilator device that is easy and fast to use, offers minimum risk of damage to the eye and is reliable in that its performance is predictable and consistent.

It is an object of the present invention to provide a device for dilating a pupil and/or maintaining a pupil in a dilated state which overcomes or ameliorates one or more of the deficiencies of the prior art or at least offers useful alternative thereto.

According to the invention there is provided a pupil dilating device for dilating a pupil and/or maintaining a pupil in a dilated state, said device being generally hooked shaped in plan view so as to define an open ended arcuate iris engaging body portion having a distal free end, and at or adjacent the other of said ends an integral positioning arm extending outwardly in a generally radial direction therefrom, the positioning arm being sized to extend in use beyond the outer periphery of the iris, said body portion including an iris engaging formation or formations being adapted to engage and retain the inner peripheral edge of an iris in an expanded state and at least one instrument engaging formation at or adjacent said distal free end to enable contraction of the body portion to facilitate engaging location within the iris.

In this manner the pupil dilating device according to the invention provides an instrument which can be easily inserted into the anterior chamber of the eye by 'dialling' through an incision in the cornea sclera or limbus, the integral arm providing remote means for assisting in the "dialling" in procedure and subsequent positioning and removal of the device from the pupil. The arm also provides means for securing the device in the preferred location and, if necessary, convenient means for rotating the dilator to a preferred orientation to enable unobstructed access for the various surgical instruments as required.

In preferred forms, the iris engaging formation or formations extend along a majority of the arcuate body portion.

Preferably, the body portion includes additional instrument engaging formations including, in particular, one such formation located at or adjacent the join between the body portion and the integral positioning arm.

Desirably, the iris engaging formations are provided by a body portion that is generally "U"-shaped in cross section along all or at least at regular intervals around its periphery, the materials and wall thicknesses ideally being selected to ensure adequate flexibility.

Preferably the body portion and/or engaging formations extend circumferentially to define an included angle of between 270° and 320°.

Desirably, the instrument engaging formations comprise fenestrations formed in an upper or anterior surface of the body portion which are adapted to receive and incorporate suitable positioning instruments such as "Sinskey" or "Fenzl" hooks or the like.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to".

In preferred forms of the invention, the positioning arm is sized to extend in use not only beyond the outer periphery of the iris, but to a position external to the eye itself, and more preferably includes a fixation point at or adjacent its distal end. Desirably, the positioning arm is curved to correspond with the contours of the relevant parts of the eye between the external curvature of the globe and the pupillary opening.

In some embodiments, it will be convenient to include a structure at the distal end of the arm to prevent the distal end of the arm from entering the wound.

It is further preferred that the iris engaging formations of the body portion comprise anterior and posterior flanges connected by an intermediate central wall or bight portion. More preferably, one or both of these flanges are scalloped to provide additional flexibility and assist in the engagement with the iris.

In some preferred embodiments, the posterior flange is more soft and supple than the anterior flange. In these embodiments the relatively supple posterior flange may be co-molded from a suitable soft material A suitable soft material is typically a biocompatible smooth material with a hardness about Shore 65A whereas the remainder of the body portion material has a hardness of about Shore 95D. Instead of co-molding, the posterior flange may be coated with a suitable soft material such as silicone or subject to a surface softening treatment such as chemical or plasma surface modification. Alternatively, the entire body portion or device may be coated with soft material. It is also envisaged that the device may be formed from a suitably soft material with an insert or other reinforcing element providing the necessary rigidity.

Embodiments using a relatively soft posterior flange provide significant benefits during procedures such as non-cataract surgery wherein the existing lens may be clear and inappropriate for removal but unable to focus adequately. The surgical insertion of an intra-ocular contact lens into the posterior chamber in front of the natural lens to correct the defect is not undertaken today if the pupil does not dilate with drugs to at least a 5 mm diameter. The present device can be used to sufficiently dilate the iris and in these particular cases, it is important to minimise trauma to the lens and capsule caused by the dilator. A relatively soft posterior flange helps to ensure this while the rest of the body portion is sufficiently rigid to maintain the pupil in a dilated state.

It is further preferred that the device be constructed so as to have a specific gravity equal to or less than balanced salt solutions so that in use it will not "weigh down" the iris.

A preferred embodiment of the invention will now be described, by way of example only, with reference to the accompanying drawings in which:

FIG. 4 is a plan view showing the device according to the invention inserted within an eye; and FIG. 5 is a sectional side view taken on line 5—5 of FIG. 4.

Figure 1:
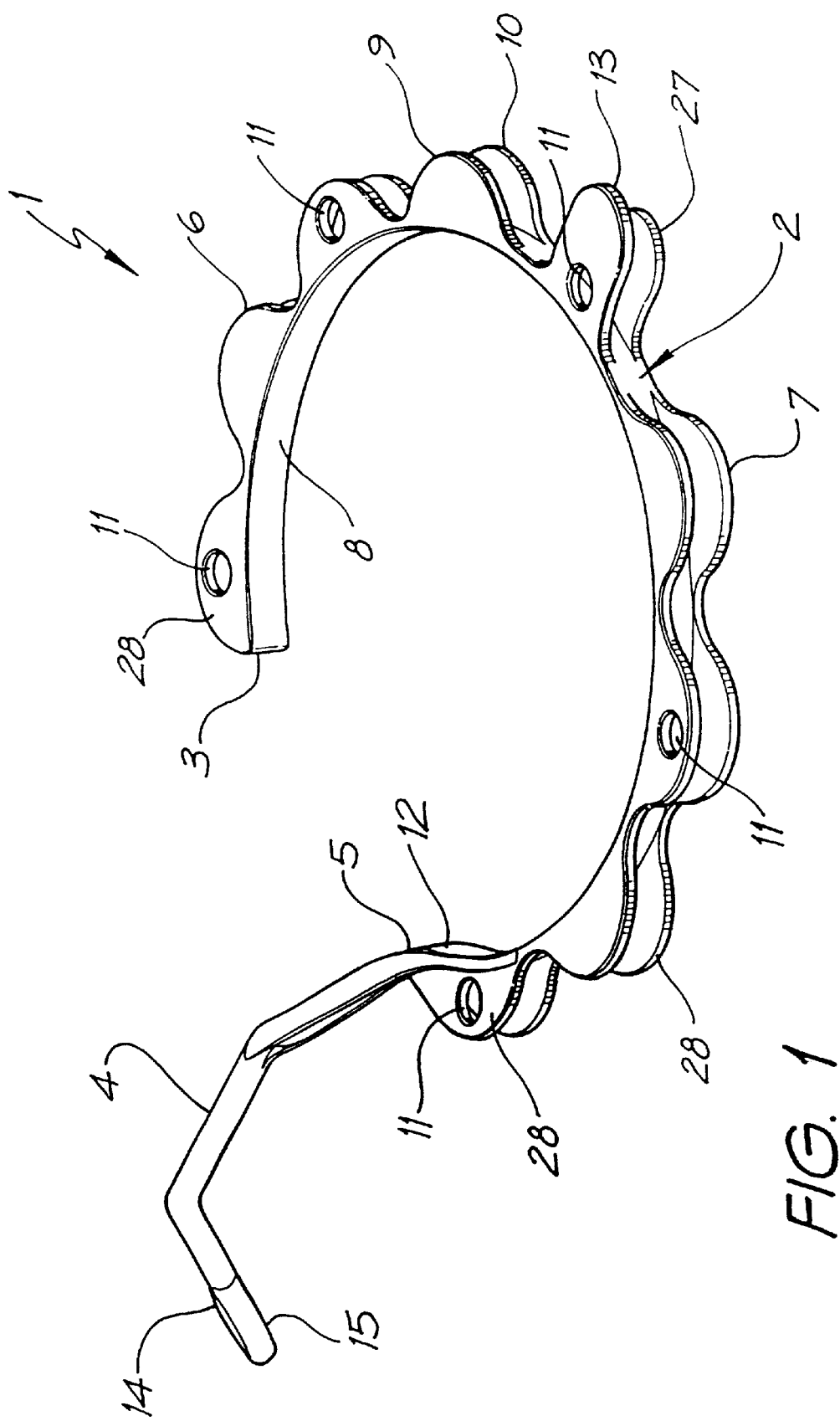
FIG. 1 is a perspective view of a first embodiment pupil dilating device according to the invention.
Figure 2:
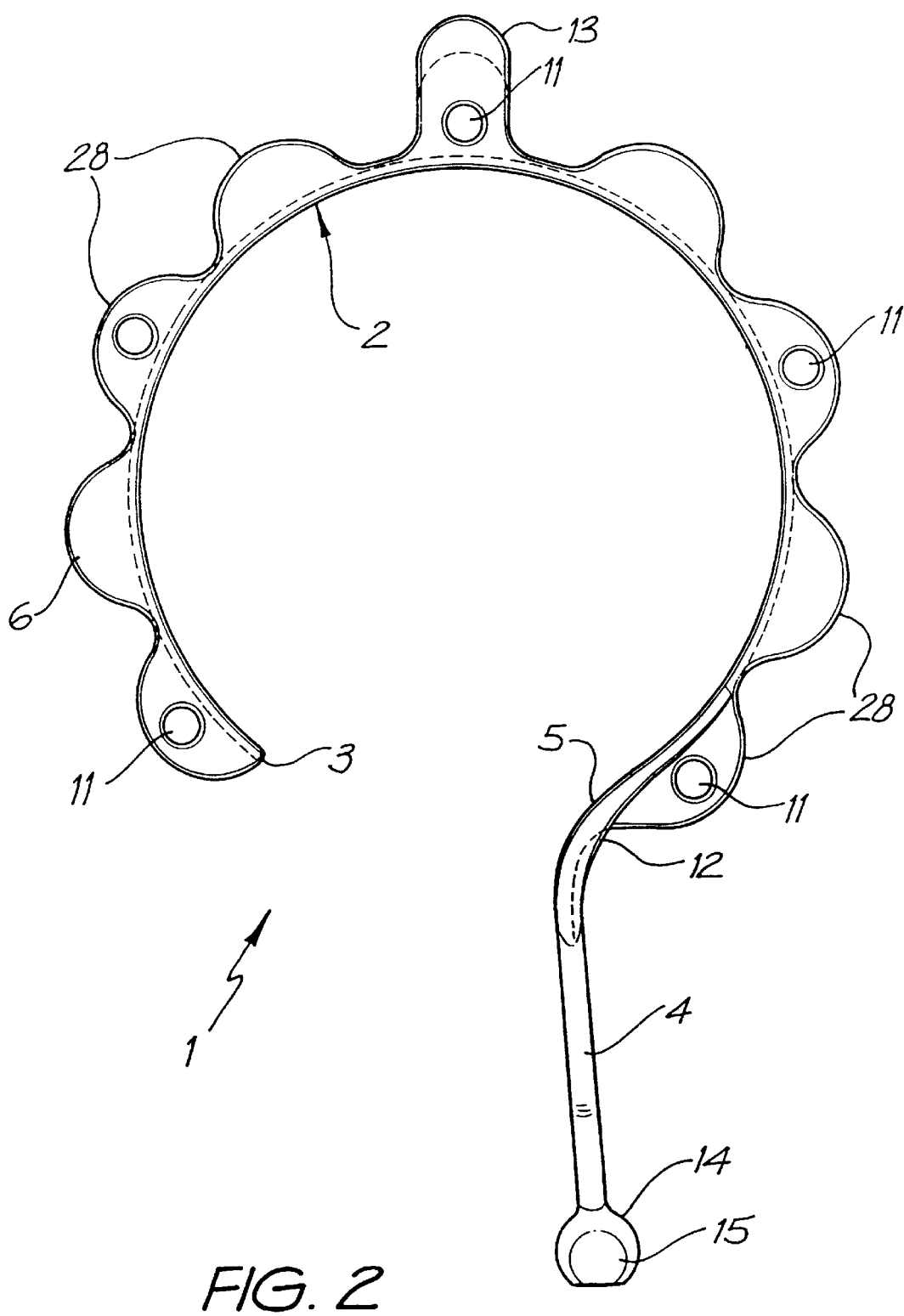
FIG. 2 is a top plan view of the pupil dilating device shown in FIG. 1.

Referring to the drawings, there is shown a pupil dilating device 1 in accordance with the invention. The device 1 is generally hook shaped in plan view (as can be seen best in FIG. 2), so as to define an open ended arcuate iris engaging body portion 2. The body portion has a distal free end 3 and an integral positioning arm 4 that extends from a position at or adjacent the other end 5 of the body 2.

The body portion 2 also includes iris engaging formations which in the preferred form illustrated comprises an anterior flange 6 and a posterior flange 7 that are connected by an intermediate central wall 8 so as to define a body portion that is generally "U"-shaped in cross section.

In the embodiment described, the anterior and posterior flanges 6 and 7 are both scalloped at their outer peripheral edges 9 and 10 to help in providing overall flexibility to the body portion and to assist in engagement of the peripheral sphinctal edge of the iris within the "W"-shaped body portion.

The anterior flange 6 includes a plurality of instrument engaging formations in the form of fenestrations 11 extending through the anterior flange that are sized to receive the tip of an appropriate positioning device such as the commonly used "Sinskey" or "Fenzl" hooks. At least one of these fenestrations 11 is located at or adjacent the distal free end 3 of the body portion 2 and another is ideally located at or adjacent the juncture 12 between the other end 5 of the body portion and the integral positioning arm 4.

Ideally, the anterior flange 6 also includes a positioning tab 13 that is preferably located on the body portion 2 at a position remote from the integral positioning arm 4. This helps to prevent the body portion 2 from slipping down in through the pupillary opening during the positioning procedure.

The device may be modified to suit non-cataract surgical procedures wherein the posterior flange 7 is relatively soft to minimise contact damage or trauma to the lens and capsule. Softening the surface of the posterior flange 7 may be achieved by any suitable means such as coating the surface with a suitable material such as a silicone, softening the surface by chemical or plasma modification or co-molding the posterior flange 7 from soft material.

To further minimise the risk of damage to the lens or capsule, the tab 27 on the posterior flange 7 opposite the positioning tab 13 on the anterior flange 6 may be reduced to the same size as the scalloped formations 28 surrounding the fenestrations 11.

If a relatively soft posterior flange 7 is not required, the dilator device 1 may be made entirely by injection molding from materials such as nylon, prolene, polyurethane, polymnethylmethacrylate, silastic, silicone polyimide, polyamide or a combination thereof, or any other material having the requisite properties of resilience, flexibility and suitability for use in surgical procedures.

Figure 3:
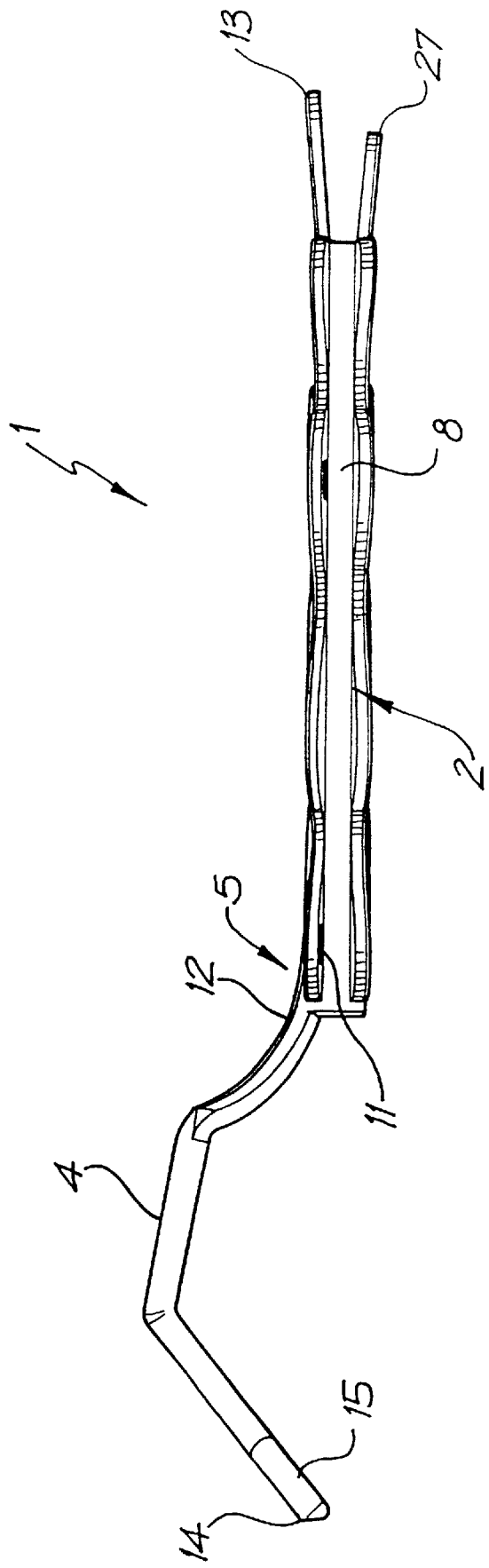
FIG. 3 is a side view of the pupil dilating device shown in the previous figures.

The integral positioning arm 4 is curved as can best be seen in the side elevation illustrated in FIG. 3 to correspond with the contours of the relevant parts of the eye between the external insertion point and the pupillary opening. Preferably, the arm 4 is of a length sufficient that its distal end remote from the iris engaging portion 2 remains, in use, external to the eye. It is also preferred that a fixation point 15 be provided at or adjacent the distal end 14 of the arm. This enables the device to be sutured to the eye (if required) to minimise movement during the surgical procedures.

Securing the positioning arm provides several important advantages during cataract surgery. As discussed above in relation to the prior art, the natural lens is broken up using an ultrasonic fractionator known as a phaco-emulsifier. The sections of the lens are then removed through the wound and any lens remnants are cleaned out by suction and irrigation/aspiration. As the positioning arm is securely held to one edge of the wound or incision in the cornea, the gap between the free end 3 and the other end 5 is conveniently held in alignment with the length of the incision. In this way access into the capsule is not hampered as can be the case with other mechanical dilator devices that are free to rotate relative to the iris. Furthermore, the inner periphery of the iris is protected by the dilator device particularly, the periphery diametrically opposed to the incision which is usually at the greatest risk of damage from contact with the tip of the phaco-emulsifler.

The distal end 14 of the positioning arm 4 may also include some type of structure which prevents the distal end from entering the wound. It is envisaged that a simple hook or barb formation would be adequate for this purpose.

The specific gravity of the device 1 as a whole can be an important consideration when selecting the appropriate material(s). If the device is too dense, it may sit too heavily on the pupil. Typically the saline solution used to irrigate the eye during use of the dilator has a specific gravity of about 1.15 to 1.2. Ideally the material(s) used to form the dilator should have a specific gravity close to that of water such that it doesn't weigh the pupil down. However, it should be noted that this preferred requirement is not essential, as it may still be possible to use higher density materials with very thin wall sections to achieve the same end.

While the device can be manufactured in any suitable size, it is currently envisaged that the device will be made in four main size categories having internal diameters of 6.5 mm, 7 mm, 7.5 mm and 8 mm. Typical dimensions for one preferred form of the invention having an internal diameter of 7 mm made from a suitable nylon, blends of suitable nylons or acrylic based multipolymers or polyurethane are set out below.

| FEATURE | DIMENSIONS |
| --- | --- |
| Internal diameter of body portion | 7 mm |
| Thickness of anterior flange | 0.13 mm |
| Thickness of posterior flange | 0.13 mm |
| Thickness of central wall portion | 0.15 mm |
| Maximum width of anterior and posterior flanges | 0.8 mm |
| Minimum width of posterior and anterior flanges | 0.13 mm |
| Radial length of tab | 1.6 mm |
| Total weight | 5 mg |
| Specific gravity | 1.2 |

Included angle of body between free end and arm ~55°

The dilator device may be clear or it may be tinted or white so as to be clearly visible during surgical procedures.

Use of the device according to the invention is very straight forward and will now be described-with reference to FIGS. 4 and 5. Firstly, an incision 16 is made in the eye 17 in the usual preferred location either in the cornea 18, sclera 19 or limbus 20, the latter being the juncture between the two other regions. This incision is usually restricted to a width of about 3 to 4 mm and is angled through the cornea into the anterior chamber so as to define an external entry wound 21 and an internal exit would 22. The anterior chamber 23 of the eye 17 is then filled in the usual manner with a visco elastic fluid to prevent the cornea collapsing and to provide lubrication and support for subsequent insertion of the dilator and surgical instruments.

Using forceps or other suitable instruments, the pupil dilating device of the invention 1 is then inserted in through the incision 16 by first inserting the dilator's distal free end 3 and then "dialling" the rest of the iris engaging body portion 2 in through the incision opening. Once the body portion is within the anterior chamber of the eye, the integral positioning arm 4 can be used to push the body portion 2 into a central position over the pupillary opening 24 such that the remote end of the body 2 having the positioning tab 13 is pushed into engagement with the sphincter of the iris 25. It is then simply a question of manipulating the positioning arm 4 and/or the body 2 (via the use of hooks through the various fenestrations 11) until the full body portion is fully engaged with the iris. Manipulation of the distal free end 3 of the body is usually achieved by inserting a hook via a further incision 26 that is usually offset at up to about 90° from the main incision 16. Once positioned, the dilator serves to retain the pupil in a dilated state and protect the pupillary opening during subsequent surgery on the interior of the eye.

When the surgical procedure is completed, removal of the device is extremely simple. In some cases the body portion can be disengaged by simply using the integral positioning arm 4 to raise the body 2 out of engagement, although in other cases it may be necessary to first dislodge the distal free end 3. Removal from the main incision 16 is then-simply the reversal of the insertion procedure.

As will be seen, the single integral arm in combination with the open ended body portion 2 provides a number of advantages over the prior art, in that insertion and removal procedures are simplified. The arm also serves to prevent the instrument from falling through the pupil or deeper into the eye and helps to facilitate the engagement and positioning of the device within the pupil. Further, the arm prevents rotation of the dilator in the eye and allows the dilator to be moved to one side of the incision 16 (as shown in FIG. 4) so that the "gap" in the body 2 is aligned with the incision to facilitate entry of instruments such as a phaco-emulsifier or I/A (Irrigation/Aspiration) Instrument.

The fixation point at the end of the arm enables the device to be sutured to the eye to minimise movement such as can happen with prior art devices during subsequent introduction of the surgical instruments into the eye.

Although the invention has been described with reference to a specific example, it will appreciated by those skilled in the field-that the invention may be embodied in many other forms.

What is claimed is:

1. A pupil dilating device for dilating a pupil and/or maintaining a pupil in a dilated state comprising:
    a body portion having an open ended arcuate iris engaging shape with a positioning end and a distal free end; and
    a single integral positioning arm attached to said positioning end and extending outwardly in a generally radial direction therefrom, the positioning arm being sized to extend in use beyond the outer periphery of the iris;
    said body portion including an iris engaging formation adapted to receive and retain the inner peripheral edge of an iris; and at least one instrument engaging formation at, or adjacent said distal free end;
    wherein said body portion and said integral positioning arm are sized and shaped for insertion in a dialing-type of motion through an incision into the eye to deploy said body in a pupil dilating position with said free distal end entering the incision first and said integral positioning arm extending outwardly of the incision.

2. The device according to claim 1 wherein the iris engaging formation or formations extend along a majority of the arcuate body portion.

3. A device according to claim 1 wherein the body portion includes additional instrument engaging formations.

4. A device according to claim 1 wherein one of said additional instrument engaging formations is located at or adjacent to the joint between the body portion and the integral positioning arm.

5. The device according to claim 1 wherein the body portion is generally "U"-shaped in cross section along all or at least at regular intervals around its periphery to provide the iris engaging formations.

6. The device according to claim 1 wherein the body portion and/or the iris engaging formations extend circumferentially to define an included angle of between 270° and 320°.

7. The device according to claim 1 wherein the instrument engaging formations comprise fenestrations formed in an upper or anterior surface of the body portion which are adapted to receive and incorporate suitable positioning instruments.

8. A device according to claim 7 wherein at least one of said instrument engaging formations with fenestrations is angularly spaced from said ends.

9. A device according to claim 1 wherein the positioning arm is sized to extend in use to a position external to the eye.

10. The device according to claim 9 wherein the positioning arm includes a fixation point at or adjacent its distal end.

11. A device according to claim 10 wherein the positioning arm is curved to correspond with the contours of the relevant parts of the eye between the external curvature of the globe and the pupillary opening.

12. A device according to claim 1 wherein the positioning arm includes a structure for preventing the distal end of the arm from entering the incision in the cornea of an eye that is used to introduce the rest of the device.

13. A device according to claim 1 wherein the iris engaging formations of the body portion comprise anterior and posterior flanges connected by an intermediate central wall or bight portion.

14. A device according to claim 13 wherein one or both of these flanges are scalloped to provide additional flexibility and assist in the engagement with the iris.

15. A device according to claim 13 or claim 14 wherein the posterior flange is more supple than the anterior flange.

16. A device according to claim 15 wherein the relatively pliable posterior flange is co-molded from a suitable soft material.

17. A device according to claim 16 wherein the suitable soft material is a biocompatible smooth material with a hardness of about Shore 65A whereas the remainder of the body portion material has-a hardness of about Shore 95D.

18. A device according to claim 15 wherein the posterior flange is coated with a suitably soft material.

19. A device according to claim 18 wherein the suitable soft material is silicone.

20. A device according to claim 18 wherein the suitable soft material is a polyurethane incorporating silicone.

21. A device according to claim 15 wherein the posterior flange is subject to a surface softening treatment such as chemical or plasma surface modification.

22. A device according to claim 14 wherein the device is coated with a suitably soft material.

23. A device according to claim 14 formed from a suitable soft material with reinforcement means for providing adequate rigidity.

24. A device according to claim 1 wherein the device is constructed so as to have a specific gravity equal.to or less than balanced salt solutions.

25. A device according to claim 1 wherein the device is tinted with a colour readily visible during surgical procedures.

26. A method of dilating an eye pupil comprising:
    providing a device with an open ended arcuate iris engaging body portion with a distal free end, and a single positioning arm attached to said body portion;
    making an incision in the eye; and
    inserting said device through said incision in a dialing-type motion with said distal free end being inserted into said incision first, to cause said body portion to engage and dilate said pupil while said single positioning arm remains outside the incision.

27. A pupil dilating device for dilating a pupil and/or maintaining a pupil in a dilated state, comprising:
    a body portion having an open ended arcuate iris engaging shape with a positioning end and a distal free end, said body portion including an iris engaging formation adapted to receive and retain the inner peripheral edge of an iris when said body portion is inserted into the eye through an incision, and at least one instrument engaging formation at, or adjacent said distal free end; and
    an integral positioning arm and extending outwardly in a generally radial direction therefrom, the positioning arm being sized to extend in use beyond the outer periphery of the iris, said integral positioning arm including a structure for preventing the distal end of the integral positioning arm from entering the incision in the cornea of the eye that is used to introduce the rest of the device.

28. A pupil dilating device for dilating a pupil and/or maintaining a pupil in a dilated state, comprising:
    a body portion having an open ended arcuate iris engaging shape with a positioning end and a distal free end, said body portion including an iris engaging formation adapted to receive and retain the inner peripheral edge of an iris when said body portion is inserted into the eye through an incision, said iris engaging formation including anterior and posterior flanges connected to an intermediate central wall or bight portion, and wherein said posterior flange is more supple than said anterior flange; and an integral positioning arm and extending outwardly in a generally radial direction therefrom, the positioning arm being sized to extend in use beyond the outer periphery of the iris.

29. The device of claim 28 wherein the relatively pliable posterior flange is co-molded from a suitable soft material.

30. The device of claim 29 wherein said the suitable soft material is a biocompatible smooth material with a hardness of about Shore 65A whereas the remainder of the body portion material has a hardness of about Shore 95D.

31. The device of claim 29 wherein the posterior flange is coated with a suitably soft material.

32. The device of claim 31 wherein the suitably soft material is silicone.

33. The device of claim 29 wherein the suitably soft material is a polyurethane incorporating silicone.

34. The device of claim 29 wherein the posterior flange is subject to a surface softening agent such as a chemical or plasma surface modification.

35. The device of claim 28 wherein the device is constructed so as to have a specific gravity equal to or less than balanced salt solution.

* * * * *